US008076432B2

(12) United States Patent
Dabdoub (10) Patent No.: US 8,076,432 B2
(45) Date of Patent: Dec. 13, 2011

(54) PHOSPHONIC COMPOUNDS AND METHODS OF USE THEREOF

(75) Inventor: Atif Dabdoub, Atlanta, GA (US)

(73) Assignee: Unichem Technologies, Inc., Atlanta, GA (US)

( * ) Notice: Subject to any disclaimer, the term of this patent is extended or adjusted under 35 U.S.C. 154(b) by 566 days.

(21) Appl. No.: 12/207,945

(22) Filed: Sep. 10, 2008

(65) Prior Publication Data

US 2009/0005527 A1   Jan. 1, 2009

Related U.S. Application Data

(63) Continuation-in-part of application No. 10/886,406, filed on Jul. 7, 2004, now Pat. No. 7,442,831.

(51) Int. Cl.
*C08F 230/02* (2006.01)

(52) U.S. Cl. ..... 526/278; 526/287; 526/288; 526/303.1; 526/304; 526/308; 526/318.2

(58) Field of Classification Search .................. 526/278, 526/287
See application file for complete search history.

(56) References Cited

U.S. PATENT DOCUMENTS

| | | | | |
|---|---|---|---|---|
| 2,365,466 A | * | 12/1944 | Hamilton | 562/816 |
| 2,439,214 A | * | 4/1948 | Lindsey, Jr. | 526/278 |
| 2,632,768 A | | 3/1953 | Coover, Jr. et al. | |
| 3,276,868 A | * | 10/1966 | Uhlig | 430/60 |
| 3,297,663 A | * | 1/1967 | Hedrbst et al. | 526/86 |
| 3,613,788 A | | 10/1971 | Kautsky | |
| 3,619,427 A | | 11/1971 | Kautsky | |
| 3,641,202 A | | 2/1972 | Biranowski et al. | |
| 3,738,937 A | | 6/1973 | Kautsky | |
| 3,763,122 A | * | 10/1973 | Elfers | 526/278 |
| 3,837,803 A | | 9/1974 | Carter et al. | |
| 3,887,340 A | | 6/1975 | Hsu et al. | |
| 4,046,707 A | | 9/1977 | Smith et al. | |
| 4,132,526 A | | 1/1979 | Schwarz et al. | |
| 4,190,615 A | | 2/1980 | Becker | |
| 4,201,669 A | | 5/1980 | Becker et al. | |
| 4,237,005 A | | 12/1980 | Becker | |
| 4,267,125 A | | 5/1981 | Dursch et al. | |
| 4,342,733 A | | 8/1982 | Steelhammer et al. | |
| 4,387,027 A | | 6/1983 | May et al. | |
| 4,409,192 A | | 10/1983 | Lichtner et al. | |
| 4,446,028 A | * | 5/1984 | Becker | 210/697 |
| 4,446,046 A | | 5/1984 | Becker | |
| 4,681,686 A | | 7/1987 | Richardson et al. | |

(Continued)

FOREIGN PATENT DOCUMENTS

EP            643081 A1 *  3/1995

OTHER PUBLICATIONS

Kojima et al. Synthesis, vol. 2, 1979, 147-148.*

(Continued)

*Primary Examiner* — David W Wu
*Assistant Examiner* — Vu A Nguyen
(74) *Attorney, Agent, or Firm* — Gardner Groff Greenwald & Villanueva, P.C.

(57) ABSTRACT

Described herein are methods for producing phosphonic compounds and compounds thereof. Stable compositions of unsaturated phosphonic acid monomers are also described. Additionally, the synthesis and use of new polymers produced from phosphonic acid monomers are presented.

15 Claims, 2 Drawing Sheets

U.S. PATENT DOCUMENTS

| | | |
|---|---|---|
| 4,900,451 A | 2/1990 | Michael et al. |
| 4,997,523 A | 3/1991 | Pease et al. |
| 5,109,033 A * | 4/1992 | Grey et al. .................. 521/147 |
| 5,116,882 A * | 5/1992 | Grey et al. .................. 521/147 |
| 5,180,498 A | 1/1993 | Chen et al. |
| 5,256,808 A | 10/1993 | Alexandratos |
| 5,281,631 A | 1/1994 | Horwitz et al. |
| 5,328,958 A * | 7/1994 | Guo et al. .................. 525/187 |
| 5,350,536 A | 9/1994 | Chen et al. |
| 5,376,731 A | 12/1994 | Kerr et al. |
| 5,439,999 A * | 8/1995 | Archer et al. .................. 526/278 |
| 5,489,616 A * | 2/1996 | Park et al. .................. 521/32 |
| 5,519,102 A | 5/1996 | Cady et al. |
| 5,582,737 A | 12/1996 | Gula et al. |
| 5,596,130 A | 1/1997 | Wright et al. |
| 5,684,104 A * | 11/1997 | Funk et al. .................. 526/232.3 |
| 5,854,080 A | 12/1998 | Harvey |
| 5,990,255 A * | 11/1999 | Priddy et al. .................. 526/193 |
| 7,150,319 B2 * | 12/2006 | Heier et al. .................. 166/263 |
| 7,420,081 B2 | 9/2008 | Dabdoub |
| 7,442,831 B2 | 10/2008 | Dabdoub |
| 2003/0149210 A1 * | 8/2003 | Hurtevent et al. .................. 526/278 |

OTHER PUBLICATIONS

Kabanov et al. Journal of Applied Polymer Science, vol. 24, 259-267 (1979).*

Ohms et al., "Synthesis and 31P and 13C NMR Studies of Pyrophosphonic Acids", Phosphorus, Sulfur, and Silicon, 1992, vol. 68, pp. 77-89.

Patent abstract of Japan and machine generated English translation of JP 05-086081, published Jun. 4, 1993.

* cited by examiner

PHOSPHONIC COMPOUNDS AND METHODS OF USE THEREOF

IN THE CROSS-REFERENCE TO RELATED APPLICATIONS

This application is a continuation-in-part of U.S. application Ser. No. 10/886,406, filed Jul. 7, 2004, which is hereby incorporated herein by reference in its entirety for all purposes.

BACKGROUND

Polyphosphonic acids have numerous applications in industry. For example, polyphosphonic acids can be used as corrosion inhibition agents in cooling water and boiler water systems (U.S. Pat. Nos. 4,446,046 and 4,201,669) and inhibitors of fouling deposit formation on jet engine components during the combustion of finished turbine combustion fuel oils (U.S. Pat. No. 5,596,130). One approach to the synthesis of polyphosphonic acids involves the radical polymerization of unsaturated phosphonic acid monomers (U.S. Pat. Nos. 4,201,669, 4,446,046 and 5,519,102).

An unsaturated phosphonic acid monomer that has received considerable attention is isopropenylphosphonic acid, which has the formula $H_2C\!\!=\!\!C(CH_3)(PO_3H_2)$, which is referred to herein as "IPPA." IPPA is currently prepared by reacting $PCl_3$ with acetic acid and acetone (U.S. Pat. No. 4,446,046). This process, however, possesses numerous disadvantages. First, $PCl_3$ is an extremely corrosive, hazardous, and toxic chemical. It requires special handling starting from transportation to storage to delivery to reactors. Any release of $PCl_3$ would require immediate evacuation. Second, the process produces HCl and acetyl chloride, which are also very hazardous and volatile by-products. The process is further complicated since these by-products come out as a mixture and have to be scrubbed by water. This dilution magnifies the quantity of these by-products and leaves a mixture of HCl and acetyl chloride in water. Finally, $PCl_3$ and the reaction by-products are very corrosive and require special equipment such as glass-lined reactors, condensers, scrubbers, collection tanks, etc. The use of $PCl_3$ requires the use of equipment that is non-reactive with chlorides. Thus, equipment composed of other materials such as stainless steel cannot be used in the production of IPPA, which reduces large-scale commercial production capabilities.

Thus, it is desirable to have a process that produces phosphonic compounds that are precursors to polyphosphonic compounds on large scale that do not require the use of $PCl_3$ and/or specialized equipment such as glass-lined reactors and accessories, etc. It would also be advantageous not to produce toxic, corrosive, and hazardous by-products during the synthesis of the phosphonic compound. Finally, it would be desirable to produce phosphonic compounds on commercial scale without special equipment such as glass-lined reactors. The methods described herein accomplish these goals.

SUMMARY

Described herein are methods for producing phosphonic compounds and compounds thereof. Stable compositions of unsaturated phosphonic acid monomers are also described. Additionally, the synthesis and use of new polymers produced from phosphonic acid monomers are presented. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted aryl group" means that the aryl group can or can not be substituted and that the description includes both an unsubstituted aryl group and an aryl group where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Variables such as m, n, X, Z, and $R^1$-$R^{12}$ used throughout the application are the same variables as previously defined unless stated to the contrary.

The term "alkyl group" as used herein is a branched- or straight-chain saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "heteroalkyl group" is defined as an alkyl group defined above having at least one heteroatom incorporated within the alkyl group. In certain embodiments, one of the hydrogen atoms can be substituted with a group having a heteroatom. For example, the group can be a hydroxyl group (OH) or thiol group (SH). Other examples of groups containing one or more heteroatoms include nitro, amino, ester, carboxylic acid, carbamide, alkoxy, or $SO_2R$ or $S(O)_2OR$, where R can be hydrogen or an alkyl group described above. Alternatively, one of the carbon atoms of the alkyl group can be substituted with a heteroatom. Examples of heteroatoms include, but are not limited to, nitrogen, oxygen, sulfur, and phosphorous.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, alkoxy, or $SO_2R$ or $S(O)_2OR$, where R can be hydrogen or an alkyl group described above. The aryl group also includes aralkyl such as, for example, benzyl. The aryl group of the aralkyl group can be substituted with one or more groups listed above.

The term "protecting group" as used herein is a group that can be chemically bound to an oxygen atom, and subsequently removed (either chemically, in-vitro, or in-vivo) from the oxygen atom by predictable methods. Examples of many of the possible protective groups can be found in *Protective Groups in Organic Synthesis* by T. W. Green, John Wiley and Sons, 1981, which is incorporated herein by reference in its entirety.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Described herein are methods for producing phosphonic compounds. In one aspect, a method for making the phosphonic compound involves reacting compounds I, II, and III

I

II

III wherein $R^1$-$R^7$ can be, independently, hydrogen, an alkyl group, a cycloalkyl group, a heterocycloalkyl group, an aryl group, a heteroaryl group, a heteroalkyl group, a protecting group, or $R^2$ and $R^4$ form a substituted or unsubstituted cycloalkyl group, or a combination thereof.

The selection of compounds I, II, and III will vary depending upon reaction conditions and the desired phosphonic compound to be produced. In one aspect, with respect to compound I, $R^1$ and $R^7$ can be, independently, hydrogen, an alkyl group, a cycloalkyl group, a heterocycloalkyl group, a heteroalkyl group, an aryl group, a heteroaryl group, a protecting group, or a combination thereof. In another aspect, $R^1$ and $R^7$ in formula I are hydrogen. This compound ($H_3PO_3$) is referred to as phosphorous acid or phosphonic acid, which is a dry, anhydrous, crystalline solid and much easier to handle when compared to $PCl_3$. Indeed, phosphonic acid is more environmentally friendly and substantially more stable than $PCl_3$, and can be transported in bags to storage or to the reactor. In a further aspect, $R^1$ and $R^7$ can be, independently, methyl, ethyl, propyl, isopropyl, butyl, pentyl, or hexyl. In the case when $R^1$ and $R^7$ are methyl, the compound is dimethyl hydrogen phosphite. In another aspect, $R^1$ and $R^7$ can be aryl groups such as phenyl or cycloalkyl groups.

In one aspect, $R^2$-$R^4$ of formula II can be, independently, hydrogen, an alkyl group, a cycloalkyl group, a heteroalkyl group, a heterocycloalkyl group, an aryl group, a heteroaryl group, a protecting group, or a combination thereof. In one aspect, $R^2$ and $R^3$ in formula II is hydrogen. In another aspect, $R^2$ and $R^3$ in formula II are hydrogen and $R^4$ can be a branched- or straight-chain alkyl group such as, for example, methyl, ethyl, propyl, isopropyl, butyl, pentyl, or hexyl. In another aspect, $R^2$ and $R^3$ in formula II are hydrogen and $R^4$ can be an aryl group or a heteroaryl group such as, for example, a phenyl group. In another aspect, compound II can be acetone, methylphenyl ketone ($R^2$ and $R^3$ are hydrogen, $R^4$ is phenyl), sulfonated benzyl methyl ketone ($R^2$ and $R^3$ are hydrogen, $R_4$ is $CH_2-C_6H_4$-p-$SO_2OH$), or ethanal ($R^2$, $R^3$, and $R^4$ are hydrogen).

In one aspect, formula II can have the formula where m is an integer from 0 to 10, $R^{12}$ is an alkyl group, and Z is a group having at least one heteroatom such as, for example, hydroxyl, thiol, nitro, amino, ester, carboxylic acid, carbamide, alkoxy, or $SO_2R$ or $S(O)_2OR$, where R can be hydrogen or an alkyl group described above. In one aspect, $R^{12}$ is methyl, m is one to three carbon atoms, and Z is a hydroxyl, thiol, or amino group.

In another aspect, $R^2$ and $R^4$ in formula II can form a substituted or unsubstituted cycloalkyl group. For example, formula II can be cyclopropenone, cyclobutanone, cyclopentanone, or clyclohexanone. The cyclic groups can be substituted with a variety of groups such as, for example, alkyl, alkenyl, alkynyl, carboxyl, amide, nitro, $SO_3H$, and the like.

In one aspect, $R^5$ and $R^6$ of formula III can be, independently, hydrogen, an alkyl group, a cycloalkyl group, a heteroalkyl group, a heterocycloalkyl group, an aryl group, a heteroaryl group, a protecting group, or a combination thereof. In one aspect, $R^5$ and $R^6$ can be, independently, a branched- or straight-chain alkyl group such as, for example, methyl, ethyl, propyl, isopropyl, butyl, pentyl, or hexyl. In another aspect, formula III can be acetic anhydride, propionic anhydride, or butyric anhydride.

The reaction for producing the phosphonic compound can optionally be performed in the presence of a catalyst. In one aspect, the catalyst can facilitate the formation of the phosphonic compound. In another aspect, a compound having the formula $R^8COOH$, wherein $R^8$ can be $C_1$-$C_8$ branched- or straight-chain alkyl such as, for example, methyl, ethyl, propyl, isopropyl, butyl, pentyl, or hexyl can be used as the catalyst. Not wishing to be bound by theory, it is believed that the catalyst can solubilize one or more intermediates that ultimately lead to the production of the phosphonic compound. The catalyst can be added to the reaction as a separate component or can be produced in situ. For example, when compound I is phosphorous acid, compound II is acetone, and compound III is acetic anhydride, glacial acetic acid is produced during the reaction. In this example, the glacial acetic acid can be isolated and sold commercially or used in future reactions.

The amount of components I, II, and III can vary depending upon the compounds selected and reaction conditions. In one aspect, the amount of component I is from 10% to 25%, 15% to 25%, or 15% to 20% by weight, the amount of component II is from 10% to 25%, 15% to 25%, or 15% to 20% by weight, and the amount of component III is from 10 to 70%, 20% to 60%, or 30% to 60%, by weight, wherein the sum of components I-III is 100%. When a catalyst is used, in one aspect, the amount of catalyst is from 1% to 50%, 5% to 40%, 5% to 30%, or 5% to 25% by weight, wherein the sum of components I-III and the catalyst is 100%. Components I-III and the optional catalyst can be added to one another in any order using the methods described herein. This is not the case when $PCl_3$ is used as the starting material. For example, in U.S. Pat. No. 4,446,046 (the '046 patent), the addition of acetic acid to $PCl_3$ is very dangerous and can be explosive if performed on a large scale. The methods described herein do not use $PCl_3$ and, thus, this is not an issue. In one aspect, components I, III, and the catalyst are mixed with one another followed by the addition of component II.

The reaction time and temperature can vary as well depending upon the selection of components I-III. In one aspect, the reaction temperature can range from 10° C. to 200° C., 10° C. to 190° C., 10° C. to 180° C., 15° C. to 180° C., 15° C. to 170° C., 15° C. to 160° C., or 15° C. to 150° C. Reaction temperatures can fluctuate during the reaction depending upon the selection of components I-III. In one aspect, the rate of addition of component II can vary in order to control the temperature of the reaction.

In one aspect, the reaction time can be from 3 minutes to 10 hours, 10 minutes to 8 hours, 10 minutes to 6 hours, 10 minutes to 4 hours, 10 minutes to 2 hours, 10 minutes to 1 hour, or 30 minutes to 1 hour. The reaction times using the methods described herein are generally much lower than processes that use $PCl_3$. For example, IPPA can be produced from phosphorous acid, acetone, and acetic anhydride with acetic acid as the catalyst in approximately 5 hours. Conversely, if IPPA is produced from $PCl_3$ using the process in the '046 patent, the reaction can take from 25 to 44 hours. One reason why the process in the '046 patent is substantially longer than those described herein is that this process produces HCl and acetyl chloride, which are very toxic and have to be removed by vacuum. HCl and acetyl chloride are the two by-products that are produced when $PCl_3$ is used. As long as $PCl_3$ is being added, these by-products will continue to come out of the reactor and need to be quickly removed under atmospheric pressure or under vacuum. This can jeopardize the reaction, because the starting materials could be volatile and removed from the reaction when the by-products are removed. This is not the case with the present invention, where HCl and acetyl chloride are not produced.

The methods described herein can be performed using readily available equipment and do not require special equipment or handling as required in the process disclosed in the '046 patent. For example, the process disclosed in the '046 patent requires glass-lined reactors, special collection tanks, and scrubbing systems to capture the HCl and acetyl chloride. The methods described herein permit the use of equipment such as, for example, stainless steel reactors, and normal collection tanks and condensers, which are widely available, much less expensive, and easier to operate and maintain. Thus, the methods described herein permit the large-scale production of phosphonic compounds in a commercially practical way.

In one aspect, the phosphonic compounds produced by the methods described have the formula IV wherein $R^1$-$R^4$ and $R^7$ can be, independently, hydrogen, an alkyl group, a cycloalkyl group, a heterocycloalkyl group, an aryl group, a heteroalkyl group, a heteroaryl group, a protecting group, or a combination thereof, or $R^2$ and $R^4$ can form a substituted or unsubstituted cycloalkyl group. In one aspect, $R^4$ in formula IV is not an alkyl group. The compounds represented in formula IV are referred to herein as unsaturated phosphonic compounds. In one aspect, $R^2$ and $R^3$ in formula IV can be hydrogen. In another aspect, $R^4$ in formula

IV can be an aryl group or a heteroaryl group. In another aspect, $R^1$ and $R^7$ in formula IV can be hydrogen. In another aspect, the compound having the formula IV has the formula $H_2C=C(R^9)(PO_3H_2)$, where $R^9$ can be hydrogen, substituted or unsubstituted phenyl, or substituted or unsubstituted benzyl (e.g., $CH_2C_6H_4$-p-$S(O)_2OH$).

In one aspect, the phosphonic acid compound has the formula XXV

XXV where $R^2$ and $R^4$ are, independently, hydrogen, an alkyl group, an aryl group, a heteroaryl group, a cycloalkyl group, a heteroalkyl group, a heterocycloalkyl group, a protecting group, or any combination thereof. In certain aspects, compounds having the formula XXV can be a mixture of monomers and dimers as described above. The compounds having the formula XXV can be produced from starting materials having the formula XXVI,

XXVI where $R^2$ and $R^4$ are defined above. In one aspect, the precursor to the phosphonic acid compounds can be the following compounds:

where $R^4$ is defined above and R is hydrogen or an alkyl group. Based on these starting materials, the following phosphonic acid compounds can be produced by the methods described herein:

The cyclic groups can be substituted with a variety of groups such as, for example, alkyl, alkenyl, alkynyl, carboxyl, amide, nitro, and the like. For example, the cyclohexyl ring above has a $SO_3H$ group attached to it.

In one aspect, the phosphonic compounds produced by the methods described have the formula VII

VII wherein $R^1$-$R^4$ can be, independently, hydrogen, an alkyl group, a cycloalkyl group, a heterocycloalkyl group, an aryl group, a heteroalkyl group, a heteroaryl group, a protecting group, or a combination thereof, or $R^2$ and $R^4$ can form a substituted or unsubstituted cycloalkyl group. The compounds represented in formula VII are dimers of the compounds having the formula IV. In one aspect, $R^2$ and $R^3$ in formula VII can be hydrogen. In another aspect, $R^4$ in formula VII can be an aryl group or a heteroaryl group. In another aspect, $R^1$ in formula VII can be hydrogen.

In another aspect, the phosphonic compounds produced by the methods described herein have the formula V

V wherein $R^1$-$R^5$ and $R^7$ can be, independently, hydrogen, an alkyl group, a cycloalkyl group, a heteroalkyl group, a heterocycloalkyl group, an aryl group, a heteroaryl group, a protecting group, or a combination thereof, or $R^2$ and $R^4$ in formula V can form a substituted or unsubstituted cycloalkyl group. In another aspect, the phosphonic compounds produced by the methods described herein have the formula VI

VI wherein $R^1$-$R^5$ and $R^7$ can be, independently hydrogen, an alkyl group, a cycloalkyl group, a heteroalkyl group, a heterocycloalkyl group, an aryl group, a heteroaryl group, a protecting group, or a combination thereof, or R² and R⁴ in formula VI can form a substituted or unsubstituted cycloalkyl group.

Compounds having the formula V and VI are precursors to the unsaturated phosphonic compounds IV and VII, respectively. For example, compound IV is produced if R⁵C(O)OH is eliminated from compound V. Similarly, compound VII is produced from compound VI with the loss of two equivalents of R⁵C(O)OH. Compound VI is the dimer of compound V. Depending upon reaction conditions, the selection of components I-III, and the use of a catalyst, it is possible to produce compounds IV-VII individually or as mixtures of compounds. For example, if excess acetic anhydride (compound III) is used in the reaction, that can promote formation of compound VI, which produces VII upon further processing.

Stable solutions (aqueous or organic solvent base) of monomer having the formula IV can be produced herein. In one aspect, a mixture of monomer IV and dimer VII can be treated with neat water for a sufficient time to substantially convert the dimer VII to monomer IV. In other aspects, the mixture of monomer and dimer can be added to an organic solvent followed by the addition of water to convert the dimer to monomer. The conversion can be performed at room temperature; however, warm water can be used to expedite the conversion. The term "substantially convert" as used herein means converting greater than 90%, greater than 95%, or 100% of the dimer to monomer. The conversion of the dimer to monomer can be monitored by techniques known in the art such as, for example ³¹P NMR. The conversion does not require the use of excess base, which is undesirable. By simply hydrolyzing the dimer with water to produce the corresponding monomer, stable aqueous solutions of monomer IV can be produced with extended shelf life. The solutions are stable at room temperature and can be easily stored and shipped in large drums. Concentrated solutions composed of the monomer can be produced. For example, solutions composed of 10% to 90% by weight monomer can be produced. The preparation of stable solutions of monomers having the formula IV has numerous applications, which will be discussed below.

In one aspect, the stable aqueous solutions of isopropenylphosphonic acid (IPPA) can be produced herein. IPPA is an important monomer; however, there are several reasons why IPPA has little market viability. First, as described above, the synthesis of IPPA requires the use of corrosive, hazardous, and toxic raw materials in addition to specialized glass-lined reactors and equipment. Additionally, conventional techniques for producing IPPA results in the formation of hazardous and corrosive by-products. Finally, the lack of knowledge for the chemistry of IPPA has curtailed and limited its success. Thus, the ability to produce stable compositions of IPPA provides numerous advantages.

Any of the unsaturated phosphonic compounds produced herein (compounds IV and VII) can be polymerized using techniques known in the art. For example, the techniques disclosed in the '046 patent, which is incorporated by reference for its teachings as it relates to polymerization chemistry, can be used herein to polymerize compounds having the formula IV and VII. In one aspect, the polymer is produced by polymerizing a monomer having the formula IV described above in the absence of the dimer VII, wherein the polymer is not polyisopropenylphosphonic acid.

The polymers described herein can be produced using techniques known in the art. For example, free-radical polymerization of the monomers described herein in water can produce the polymers. Examples of free radical initiators useful herein include, but are not limited to, persulfates (e.g., sodium persulfate) and azobis compounds (e.g., AIBN). In other aspects, organic phase polymerization can be performed, where the polymerization takes place in organic solvents in the presence of organic peroxides such as, for example, t-butyl hydrogen peroxide or benzoyl peroxide.

A variety of different polymers can be produced herein. For example, homopolymers can be produced. Alternatively, copolymers and terpolymers can be readily produced. For example, the polymer can be the polymerization product of two or more different monomers having the formula IV. In other aspects, the polymer can be the polymerization product between at least one monomer having the formula IV and one or more olefinically unsaturated monomers. Examples of olefinically unsaturated monomers include, but are not limited to, acrylic acid, methacrylic acid, acrylamide, t-butylacrylamide, methyl methacrylate, ethyl acrylate, 2-hydroxy ethyl acrylate, 2-hydroxy propyl acrylate, maleic acid, maleic anhydride, vinyl sulfonic acid, 2-acrylamido-2-methyl propane sulfonic acid (AMPS), styrene sulfonic acid, vinyl acetate, styrene acetate, styrene benzoic acid, vinyl cyclopropane, vinyl cyclopentane, vinyl cyclohexane, or any combination thereof.

Figure 1:
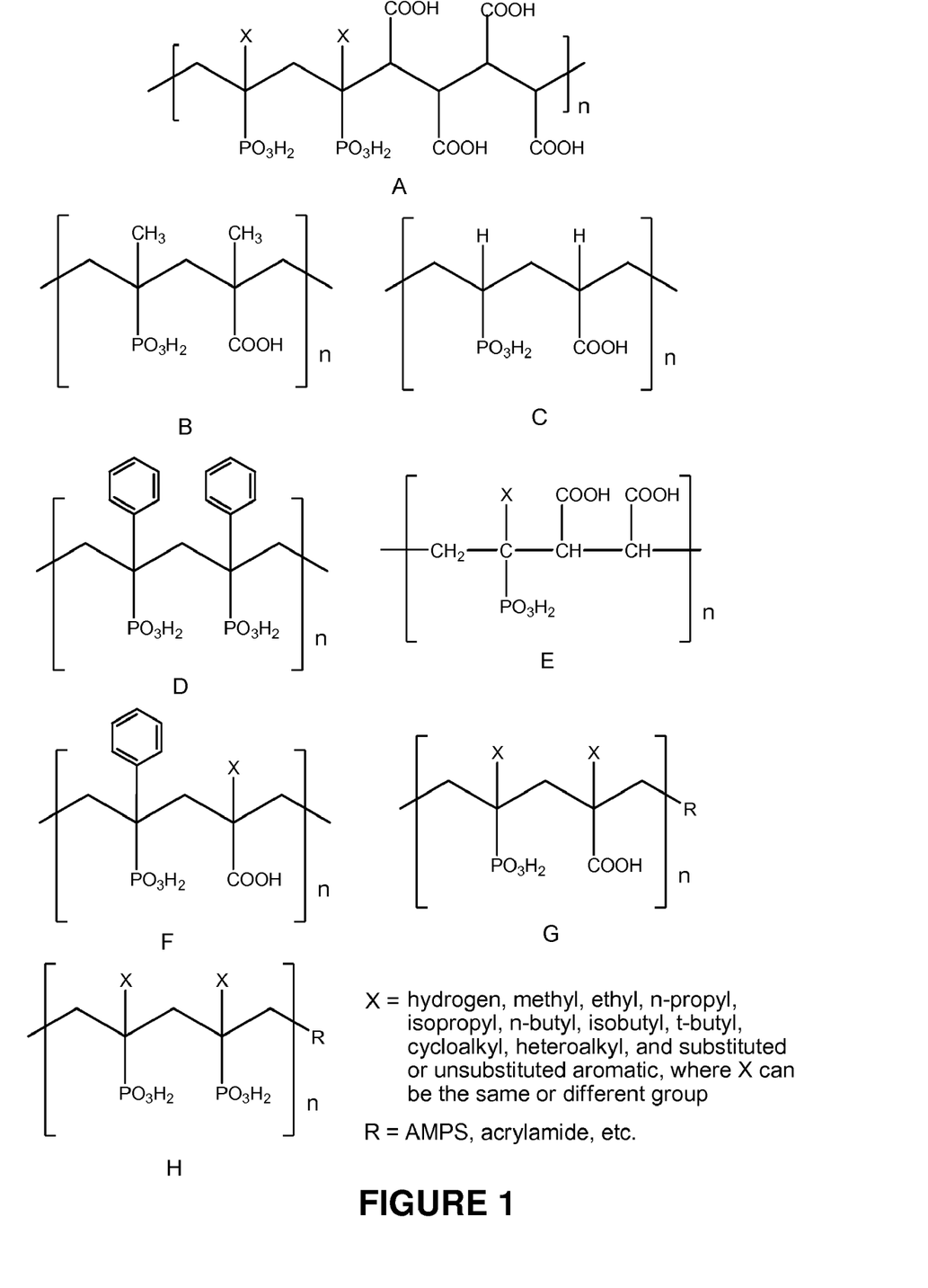
FIG. 1 shows examples of phosphonic acid polymers described herein.

Provided below are some examples of polymers described herein:

X = hydrogen, methyl, ethyl, n-propyl, isopropyl, n-butyl, isobutyl, t-butyl, cycloalkyl, heteroalkyl, and substituted or unsubstituted aromatic, where X can be the same or different group Additional structures are provided in FIG. 1. As shown in the formulae above and FIG. 1, the phosphonate and/or carboxyl functionalities are pendant to the polymer backbone. In certain aspects, it is desirable to have a polymer with a phosphonate functionality as well as a carboxylate functionality whereby both groups are pendant to the polymer backbone.

The polymers described herein have numerous applications. For example, the polymers described herein can inhibit scale formation, corrosion, or both in a system. The term "inhibit" as used herein means completely preventing scale formation and/or corrosion or reducing the rate of scale formation and/or corrosion. Scale formation is an expensive problem in many industrial systems, causing delays and shutdown for cleaning and removal. Scale formation can also lead to corrosion of system parts as well. In general, scale formation and corrosion are the result of the formation of crystalline deposits on the surface of metallic substrates that are continuously exposed to water over time. The water has one or more minerals that can form crystals on the metal substrate, which can be very difficult to remove. An example of this is calcium carbonate. Not wishing to be bound by theory, the phosphonate groups present on the polymers described herein inhibit the crystallization of calcium carbonate and inhibit scale formation and corrosion. If crystal formation does occur, the calcium carbonate crystalline lattice is generally distorted due to the presence of the polymer incorporated within the lattice. This ultimately weakens the crystal lattice (i.e., produces soft scale) and makes removal of calcium carbonate deposits much easier. In this aspect, the polymers described herein can function as hardness stabilizers. Although calcium carbonate is an example of a mineral that can result in scale formation, scale and deposits formed from calcium phosphate, calcium sulfate, calcium phosphonate, and other metal ions (e.g., iron, zinc, magnesium, etc.) can also be inhibited as well.

The presence of other groups such as carboxyl and/or sulfonic groups in the polymers described herein can also inhibit scale formation and/or corrosion. For example, sulfonic groups can increase the dispersancy of iron, which can ultimately increase the performance of the polymer by inhibiting iron poisoning. Thus, the polymers described herein can also behave as dispersants and prevent the accumulation of metal ions that can facilitate scale and sludge formation. Additionally, rust formation can be reduced by using the polymers herein as iron dispersants. Polymers containing carboxyl groups are generally good dispersants for calcium carbonate and calcium sulfate. Therefore, in certain aspects, the polymers described herein can display enhanced scale and corrosion formation by incorporating these groups into the polymers.

The polymers can be applied to any system that is subject to scale formation and/or corrosion. Examples of such systems include, but are not limited to, cooling water systems, boiler water systems, steam generating systems, sea-water evaporation equipment, reverse osmosis equipment, paper manufacturing equipment, sugar evaporation equipment, soil irrigation systems, hydrostatic cookers, gas scrubbing systems, closed circuit heating systems, agricultural based refrigeration systems, downhole wall systems, and pulp and paper mill systems.

The polymers can be applied to the systems using techniques known in the art. For example, the polymers can be applied to a substrate by spraying or dipping the substrate with an aqueous solution of the polymer. In this aspect, the polymer produces a protective layer on the surface of the substrate and prevents deposit formation. The polymers can be used in combination with other components to help inhibit scale formation and/or corrosion. Fort example, oxygen scavengers such as, for example, sodium sulfite, can be added to the polymer composition to scavenge oxygen that can contribute to corrosion or pitting problems. In other aspects, filming amines can be used in combination with the polymers to neutralize condensates as they enter the vapor phase. In general, it is not desirable to produce an acidic condensate, which creates dangerous conditions as well as contribute to corrosion and pitting problems.

In another aspect, the monomer having the formula IV can be reacted with $H_3PO_3$, a monoester of $H_3PO_3$, or a diester of $H_3PO_3$ to produce compounds having the formula X

Figure 2:
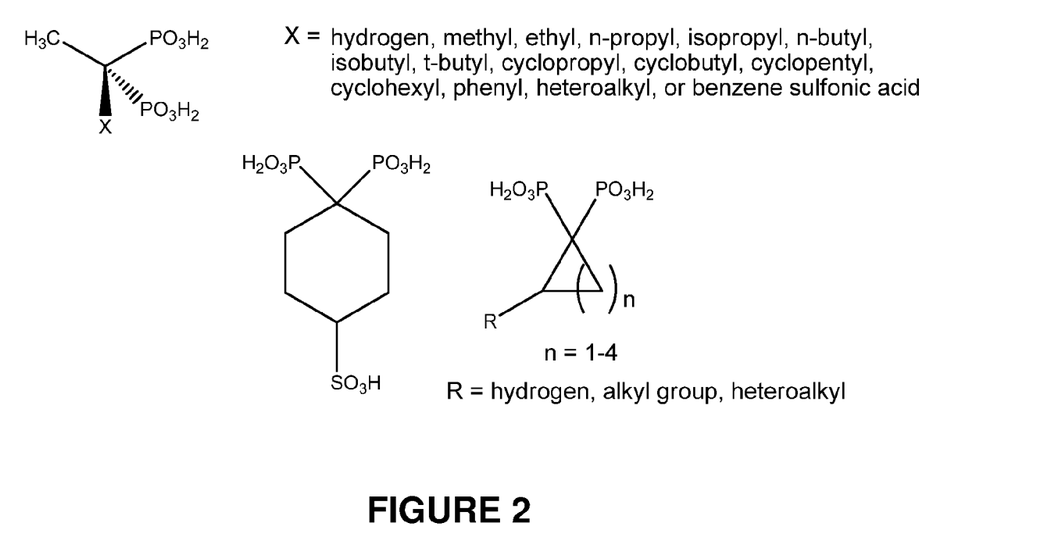
FIG. 2 shows examples of diphosphonic acid compounds described herein produced from the corresponding unsaturated phosphonic acid monomer.

X wherein $R^1$-$R^4$, $R^7$, $R^{10}$, and $R^{11}$ comprises, independently, hydrogen, an alkyl group, a cycloalkyl group, a heteroalkyl group, a heterocycloalkyl group, an aryl group, a heteroaryl group, a protecting group, or a combination thereof, or $R^2$ and $R^4$ form a substituted or unsubstituted cycloalkyl group. Although both phosphonic acid groups are attached to the same carbon atom in formula X, it is also possible to produce compounds where the phosphonic acid groups are on different carbon atoms (i.e., adjacent carbon atoms). Examples of diphosphonic acid compounds are depicted in FIG. 2. The reaction between monomer and $H_3PO_3$, a monoester of $H_3PO_3$, or a diester of $H_3PO_3$ can be performed in organic solvents. For example, the reaction can take place in a mixture of methanol and sodium methoxide. The compounds having the formula X are useful as scale inhibitors, deflocculants, sequestrants, hardness stabilizers in water treatment, and detergents.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Preparation of Isopropenylphosphonic Acid (IPPA)

To a 1.0 L, 3-necked flask equipped with a magnetic stirring bar and an addition funnel, was added 164 g (2.0 moles) of dry, anhydrous phosphorus acid. Acetic anhydride (400 g; 3.9 moles) was added followed by acetic acid (160 g; 2.6 moles). The addition funnel was removed, and the flask was then equipped with a heating mantel, magnetic stirrer, thermometer, reflux condenser, and pressure compensated addition funnel. The mixture was stirred at ambient (19° C.) temperature until a clear solution was obtained (10 min; 18° C.). Acetone (140 g; 2.4 moles) was added dropwise through the addition funnel. The temperature started to rise steadily after 3 min of acetone addition and by the time 35 g (0.6 moles after 12 min.) of acetone was added, the temperature had risen from 18° C. to 23° C. The temperature steadily rose to 40° C. by the time 105 g (1.8 moles at 32 min.) of acetone was added. Acetone addition was stopped, and the mixture was allowed to cool for 8 minutes. Acetone addition was resumed at 37° C., and it took 10 minutes to add the rest of the acetone 35 g (0.6 moles). The temperature climbed to 52° C. then completely stopped. Thus, it took 50 minutes to add all the acetone. Optionally, a balance of constant cooling and constant adding of acetone can be maintained. During acetone addition, no acetone was seen refluxing, which indicated that an immediate and stable reaction occurred. Also, the temperature only rose with each further addition of acetone and, the temperature did not rise when acetone addition stopped. The reaction showed extreme control and can be stopped at any point, if necessary. In addition, white oligomers (formula V and VI) were seen temporarily. The above mixture was allowed to stir at 50 to 60° C. (low heat was occasionally applied to maintain temperature) for one hour. Moderate heat was then applied, and the temperature was allowed to steadily rise to 100° C.

At this point, a reflux condenser was replaced by an adapter, a thermometer, and a horizontal reflux condenser that was connected to a collection flask that was connected to a trap en route to a vacuum pump. When temperature reached 118° C., distillate was allowed to collect in the flask while the temperature continued to rise to 140° C. Vacuum was then gradually applied (to prevent surge of distillate) until full vacuum was obtained. At 170° C. and full vacuum, no more distillate was produced, with a total distillate collected at 623 g (99%). This clear, colorless distillate was confirmed to be 100% pure acetic acid.

During the whole process (ca., 4½ hrs. between the addition of reactants, hold period, heating and collecting), the product mix was colorless until about 80° C. when the product turned straw-colored. At 90° C., it turned light yellow and at 110° C., it looked yellow-orange (amber), while at 140° C. it was dark amber. The final product IPPA (residue) at 170° C. was a viscous, golden-yellow liquid and weighed 234 g.

$P^{31}$ NMR showed two main peaks: one single peak at delta 20.8 PPM (29%) and one single peak at delta 10.2 PPM (71%). These peaks correspond to isopropenyl phosphonic acid monomer (IPPA) ($C_3H_7O_3P$, 29%) and isopropenyl phosphonic acid anhydride dimer (IPPAA) ($C_6H_{12}O_5P_2$, 71%).

Example 2

Large-Scale Production of Isopropenylphosphonic Acid (IPPA)

Table 1 shows the amount of starting materials used to produce IPPA on large scale using $PCl_3$ as described in Example 3 of the '046 patent while Table 2 shows the amount of by-products that would be produced from this process. Table 3 shows the amounts of starting materials used to produce IPPA using the methods described herein. Table 4 indicates that the only by-product is glacial acetic acid, which can be recovered as 100% pure acetic acid and sold in the open market.

TABLE 1

| Raw Materials | Pounds | Mol. Wt | Moles | B.P. ° C. | Gallons |
|---|---|---|---|---|---|
| Acetone | 1320 | 58.08 | 22.73 | 56.5 | 200 |
| Acetic Acid-Glacial | 6358 | 60.05 | 105.87 | 118 | 735 |
| $PCl_3$ | 3212 | 137.3 | 23.39 | 76 | 243 |
| Total | 10890 | | 152 | | 1178 |

TABLE 2

| Raw Materials | Pounds | Mol. Wt | Moles | B.P. ° C. | Gallons |
|---|---|---|---|---|---|
| Hydrochloric Acid | 1136 | 36.46 | 28.85 | — | 362 |
| Acetyl Chloride | 3060 | 78.50 | 38.98 | 52 | 333 |
| Acetic Acid | 4019 | 60.05 | 28.86 | 118 | 465 |
| Total | 8215 | | 66.92 | | 1160 |

TABLE 3

| Raw Materials | Pounds | Mol. Wt | Moles | B.P. ° C. | Gallons |
|---|---|---|---|---|---|
| Phosphorous Acid | 1918 | 82 | 23.39 | — | — |
| Acetic Anhydride | 4674 | 102 | 45.83 | 139 | 514 |
| Acetic Acid | 1871 | 60.05 | 31.16 | 118 | 216 |
| Acetone | 1638 | 58.08 | 28.21 | 56 | 248 |
| Total | 10101 | | | | 978 |

TABLE 4

| Raw Materials | Pounds | Mol. Wt | Moles | B.P. ° C. | Gallons |
|---|---|---|---|---|---|
| Acetic Acid | 7136 | 60.05 | 118.8 | 118 | 825 |

The process used in the '046 patent produces 1,160 gallons of mixed hazardous materials (HCl and acetyl chloride in acetic acid and water) (Table 2). The acetyl chloride, HCl, and acetic acid cannot be separated in actual production. Conversely, use of the process described herein produces only glacial acetic acid (Table 4, 825 gallons), which can be recovered and sold in the open market. If one million pounds of IPPA were produced using the process in the '046 patent, theoretically 406,000 gallons of HCl, acetyl chloride, and acetic acid would be produced, which would create numerous environmental and safety issues. The use of the process described herein, however, theoretically produces 289,000 gallons of glacial acetic acid, which can be recovered and sold in the open market.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A copolymer produced by the process consisting of polymerizing (1) one or more olefinically unsaturated monomers selected from the group consisting of maleic acid, maleic anhydride, t-butylacrylamide, 2-acrylamido-2-methyl propane sulfonic acid (AMPS), vinyl acetate, vinyl cyclopropane, vinyl cyclopentane, vinyl cyclohexane, and any combination thereof and (2) at least one monomer comprising the formula IV

IV wherein $R^1$-$R^4$ and $R^7$, independently, is selected from the group consisting of hydrogen, an alkyl group, a cycloalkyl group, a heteroalkyl group, a heterocycloalkyl group, an aryl group, a heteroaryl group, a protecting group, or a combination thereof, or $R^2$ and $R^4$ form a substituted or unsubstituted cycloalkyl group, wherein $R^1$-$R^4$ and $R^7$ are not simultaneously hydrogen.

2. The polymer of claim 1, wherein $R^2$ and $R^3$ are hydrogen.

3. The polymer of claim 2, wherein $R^1$ and $R^7$ are hydrogen.

4. The polymer of claim 3, wherein $R^4$ is an aryl group or a heteroaryl group.

5. The polymer of claim 3, wherein $R^4$ is a substituted or unsubstituted phenyl group or a substituted or unsubstituted benzyl group.

6. The polymer of claim 3, wherein $R^4$ is $CH_2C_6H_4$-p-$S(O)_2OH$.

7. The polymer of claim 1, wherein $R^4$ is an alkyl group.

8. The polymer of claim 7, wherein the alkyl group is selected from the group consisting of methyl, ethyl, propyl, isopropyl, butyl, isobutyl, pentyl, and hexyl.

9. The polymer of claim 1, wherein $R^4$ is a cycloalkyl group, and the cycloalkyl group is selected from the group consisting of cyclopropyl, cyclobutyl, cyclopentyl, and cyclohexyl.

10. The polymer of claim 1, wherein $R^4$ is selected from the group consisting of heptyl, octyl, decyl, tetradecyl, hexadecyl, eicosyl, and tetracosyl.

11. The polymer of claim 1, wherein at least one of $R^2$, $R^3$, or $R^4$ is selected from the group consisting of an alkyl group, a cycloalkyl group, a heterocycloalkyl group, a heteroaryl group, a protecting group, and an aryl group substituted with one or more $SO_2R$ or $S(O)_2OR$ groups, where R is hydrogen or an alkyl group.

12. A method for inhibiting scale formation in a system comprising applying to the system the polymer of claim 1.

13. A method for inhibiting corrosion in a system comprising applying to the system the polymer of claim 1.

14. A method for inhibiting corrosion and scale formation in a system comprising applying to the system the polymer of claim 1.

15. A method for making a copolymer consisting of polymerizing (1) one or more olefinically unsaturated monomers selected from the group consisting of maleic acid, maleic anhydride, t-butylacrylamide, 2-acrylamido-2-methyl propane sulfonic acid (AMPS), vinyl acetate, vinyl cyclopropane, vinyl cyclopentane, vinyl cyclohexane, and any combination thereof and (2) at least one monomer comprising the formula IV

IV wherein $R^1$-$R^4$ and $R^7$ comprises, independently, hydrogen, an alkyl group, a cycloalkyl group, a heteroalkyl group, a heterocycloalkyl group, an aryl group, a heteroaryl group, a protecting group, or a combination thereof, wherein the polymerization product is not polyisopropenylphosphonic acid.

* * * * *